(12) United States Patent
Khan et al.

(10) Patent No.: US 11,554,152 B2
(45) Date of Patent: Jan. 17, 2023

(54) ANTIVIRAL COMPOSITIONS AND METHODS OF USING SAME

(71) Applicant: The Aga Khan University, Karachi (PK)

(72) Inventors: Farhan Raza Khan, Karachi (PK); Syed Tariq Ali, Karachi (PK); Syed Murtaza Raza Kazmi, Karachi (PK)

(73) Assignee: The Aga Khan University, Karachi (PK)

( * ) Notice: Subject to any disclaimer, the term of this patent is extended or adjusted under 35 U.S.C. 154(b) by 0 days.

(21) Appl. No.: 17/127,589

(22) Filed: Dec. 18, 2020

(65) Prior Publication Data

US 2022/0133829 A1 May 5, 2022

(30) Foreign Application Priority Data

Nov. 5, 2020 (PK) .................................... 760/2020

(51) Int. Cl.

| | | |
|---|---|---|
| *A61K 36/58* | (2006.01) | |
| *A61K 36/886* | (2006.01) | |
| *A61K 9/00* | (2006.01) | |
| *A61K 9/08* | (2006.01) | |
| *A61P 31/14* | (2006.01) | |
| *A61K 47/02* | (2006.01) | |
| *A61K 47/44* | (2017.01) | |
| *A61K 47/10* | (2017.01) | |
| *A61K 47/26* | (2006.01) | |
| *A61K 9/107* | (2006.01) | |

(52) U.S. Cl.
CPC ............ *A61K 36/58* (2013.01); *A61K 9/0053* (2013.01); *A61K 9/08* (2013.01); *A61K 9/107* (2013.01); *A61K 36/886* (2013.01); *A61K 47/02* (2013.01); *A61K 47/10* (2013.01); *A61K 47/26* (2013.01); *A61K 47/44* (2013.01); *A61P 31/14* (2018.01)

(58) Field of Classification Search
CPC ........ A61K 36/58; A61K 9/0053; A61K 9/08; A61K 9/107; A61K 36/886; A61K 47/02; A61K 47/10; A61K 47/26; A61K 47/44; A61P 31/14

See application file for complete search history.

(56) References Cited

U.S. PATENT DOCUMENTS

| | | | | |
|---|---|---|---|---|
| 4,150,151 A | * | 4/1979 | Pader ..................... | A61K 8/463 424/56 |
| 2002/0091164 A1 | * | 7/2002 | Parmar .................. | C09K 23/00 516/98 |
| 2013/0243702 A1 | * | 9/2013 | Ravindran ............. | A61K 36/47 424/58 |

FOREIGN PATENT DOCUMENTS

WO  WO-2016106313 A1 * 6/2016 ............. A61K 36/28

OTHER PUBLICATIONS

Ahmad et al., "Designing and screening of universal drug from neem (*Azadirachta indica*) and standard drug chemicals against influenza virus nucleoprotein," BMC Complementary and Alternative Medicine, Dec. 2016, 16:519, 8 pages.

Ahmad et al., "Molecular docking based screening of neem derived compounds with the NS1 protein of influenza virus," Bioinformation, Jul. 2015, 11(7):359-365.

Almas, "The antimicrobial effects of extracts of *Azadirachta indica* (Neem) and *Salvadora persica* (Arak) chewing sticks," Indian J Dent. Res., 1999, 10(1):23-26.

Biswas et al., "Biological activities and medicinal properties of neem (*Azadirachta indica*)," Current Science, Jun. 2002, 82(11):1336-1345.

Bohora et al., "Comparison of the antibacterial efficiency of neem leaf extract and 2% sodium hypochlorite against E. faecalis, C. albicans and mixed culture—An in vitro study," Endodontology, 2010, 22:5 pages.

Chava et al., "The Efficacy of Neem Extract on Four Microorganisms Responsible for causing Dental Caries viz *Streptococcus mutans*, *Streptococcus salivarius*, *Streptococcus mitis* and *Streptococcus sanguis*: An in vitro Study," The Journal of Contemporary Dental Practice, Dec. 2012, 13(6):769-772.

Elavarasu et al., "Evaluation of anti-plaque microbial activity of *Azadirachta indica* (neem oil) in vitro: A pilot study," Journal of Pharmacy and Bioallied Sciences, Aug. 2012, 4:S394-S396, 4 pages.

Polaquini et al., "Effect of aqueousextract from Neem (*Azadirachta indica* A. Juss) on hydrophobicity, biofilm formation and adhesion in composite resin by Candida albicans," Archives of Oral Bioiogy, Jun. 2006, 51(6):482-490.

Rao et al., "Molecular docking based screening of novel designed chalcone series of compounds for their anti-cancer activity targeting EGFR kmase domain," Biomedical Informatics, Jul. 2015, 11(7):322-329.

Schmutterer, "Properties and potentials of natural pesticides from neem tree," Annu. Rev. Entomol, Jan. 1990, 35:271-297.

Sharma et al., "Review on neem (*Azadirechta indica*): thousand problem one solution," Int Res J Pharm., Dec. 2011, 2(12):97-102.

Siswomihardjo et al., "The difference of antibacterial effect of neem leaves and stick extracts," Int Chin J Dent, Mar. 2007, 7:27-29, 8 pages.

Subapriya et al., "Medicinal Properties of Neem Leaves: A Review." Curr. Med. Chem.—Anti-Cancer Agents, Mar. 2005, 5:149-156.

Talwar et al., "Plant immunomodulators for termination of unwanted pregnancy and for contraception and reproductive health," Immunology and Cell Biology, Dec. 1997, 75:190-192.

Wolinsky et al., "The inhibiting effect of aqueous *Azadirachta indica* (Neem) extract upon bacterial properties influencing In Vitro plaque formation," J Dent. Res, Feb. 1996, 75(2): 816-822.

Zhang et al., "Techniques for extraction and isolation of natural products: a comprehensive review," BMC Chin. Med., Apr. 2018, 13(20): 26 pages.

* cited by examiner

*Primary Examiner* — Doan T Phan

(74) *Attorney, Agent, or Firm* — Fish & Richardson P.C.

(57) ABSTRACT

The present disclosure generally relates to pharmaceutical mouth rinse compositions comprising Neem oil that are useful for treating viral infections, including coronavirus infections.

19 Claims, No Drawings

ANTIVIRAL COMPOSITIONS AND METHODS OF USING SAME

RELATED APPLICATION

This disclosure claims priority to Pakistan Patent Application No. 760/2020, entitled "Antiviral Compositions and Methods of Using Same" and filed on Nov. 5, 2020, the entire contents of which is incorporated herein by reference.

TECHNICAL FIELD

This disclosure relates to antiviral compositions and uses thereof, and more particularly to pharmaceutical mouth rinse compositions and uses of same.

BACKGROUND

Coronaviridae are positive strand RNA viruses that typically cause respiratory and enteric diseases in mammals. Coronaviruses are responsible for numerous human diseases, including severe acute respiratory syndrome (SARS) Middle East Respiratory Syndrome (MERS), and most recently Coronavirus Disease 2019 (COVID-19). These viruses are highly transmissible and may result in severe, even lethal, respiratory complications for infected subjects. See, e.g., Ksiazek et al., New Eng. J. Med. 2003, 348(20): 1947-1958 and Drosten et al., New Eng. J. Med. 2003, 348(20): 1959-1968.

At present, there are no approved antiviral drugs for coronaviruses. While coronaviruses generally cause mild to moderate infections of relatively short duration in humans (e.g., "common colds"), the incidence of disease is sufficiently high to be of economic importance, causing losses in school and workplace productivity. Accordingly, there is an urgent medical need for antiviral agents to treat and/or prevent coronavirus infections.

SUMMARY

Provided herein is a pharmaceutical mouth rinse composition comprising:
about 0.1-1.2% (w/w) Neem oil;
about 8-30% (w/w) Neem extract;
about 3-20% (w/w) *Aloe* extract;
about 0.05-0.15% (w/w) tonicity modifier; and
about 48.65-88.85% (w/w) aqueous carrier.

Also provided herein is a pharmaceutical mouth rinse composition consisting of:
about 0.1-1.2% (w/w) Neem oil;
about 8-30% (w/w) Neem extract;
about 3-20% (w/w) *Aloe* extract;
about 0.05-0.15% % (w/w) NaCl; and
about 48.65-88.85% (w/w) aqueous carrier.

Provided herein is a pharmaceutical mouth rinse composition comprising:
about 0.25% (w/w) Neem oil;
about 10% (w/w) Neem extract;
about 5% or about 10% (w/w) *Aloe* extract;
about 2-3% (w/w) polysorbate 20;
about 0.5-1.5% (w/w) propylene glycol;
about 0.09-0.1% (w/w) NaCl;
about 0.01-0.05% (w/w) menthol;
about 0.01-0.15% (w/w)thymol;
about 0.05-0.1% (w/w) eucalyptus oil;
about 0.05-0.1% (w/w) wintergreen oil; and water.

Also provided herein is a pharmaceutical mouth rinse composition consisting of:
about 0.25% (w/w) Neem oil;
about 10% (w/w) Neem extract;
about 5% or about 10% (w/w) *Aloe* extract;
about 2-3% (w/w) polysorbate 20 (w/w);
about 0.5-1.5% (w/w) propylene glycol;
about 0.09-0.1% (w/w) NaCl;
about 0.01-0.05% (w/w) menthol;
about 0.01-0.15% (w/w)thymol;
about 0.05-0.1% (w/w) eucalyptus oil;
about 0.05-0.1% (w/w) wintergreen oil; and water.

Also provided herein is a method of treating or preventing a coronaviridae infection in a subject in need thereof, comprising administering the pharmaceutical mouth rinse composition to the subject.

Also provided herein is a method of inhibiting coronaviridae replication in a subject in need thereof, comprising administering the pharmaceutical mouth rinse composition to the subject.

DETAILED DESCRIPTION

Definitions

Unless otherwise defined, all technical and scientific terms used herein have the same meaning as commonly understood by one of ordinary skill in the art to which this disclosure belongs. Methods and materials are described herein for use in the present application; other, suitable methods and materials known in the art in some aspects this disclosure are also used. The materials, methods, and examples are illustrative only and not intended to be limiting. All publications, patent applications, patents, sequences, database entries, and other references mentioned herein are incorporated by reference in their entireties. In case of conflict, the present specification, including definitions, will control.

The term "about", as used herein, is used to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "mouth rinse", as used herein, includes liquid formulations such as mouthwashes, dental rinses, mouth sprays, dental solutions, and oral irrigation fluids. Such a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity, including nasal lavage.

The term "solution", as used herein, refers to a homogeneous liquid with no visible phase separation.

The term "emulsion", as used herein, refers to a fine dispersion of minute droplets of one liquid in another in which the two liquids are immiscible.

As used herein, the term "plant extract" refers to substances with desirable properties that are removed from the tissue of a plant. Example of plant tissues include leaves, stems, roots, seeds, flowers, and fruits. Methods for the preparation of plant extracts are known to those skilled in the art, for example, decoction, maceration, solvent extraction, expeller, cold press, hot press, steam and water distillation, and percolation.

The term "tonicity modifier" refers to a substance used to adjust the total concentration of solutes in a liquid to a desired value. Examples of tonicity modifiers commonly used in the preparation of pharmaceutical compositions include, but are not limited to, sodium chloride, potassium chloride, calcium chloride, glycerin, magnesium chloride, mannitol and dextrose.

The term "buffer" refers to a mixture of a weak acid and its conjugate base, or a weak base and its conjugate acid that is used to maintain the pH of a solution at a nearly constant value. Examples of buffers commonly used in the preparation of pharmaceutical compositions include, but are not limited to, sodium phosphates, potassium phosphates, sodium citrate, citric acid, succinic acid, sodium succinate, (L)-histidine, acetic acid, sodium acetate, tartaric acid, sodium tartrate, glucuronic acid, lactic acid, (L)-aspartic acid, (L)-glutamic acid, borate, malic acid, fumaric acid and tromethamine.

As used herein, the term "flavoring agents" refer to natural or artificial substances that impart certain favorable aroma or taste. Exemplary flavoring agents include, but are not limited to, peppermint oil, corn mint oil, spearmint oil, wintergreen oil, clove bud oil, cassia, sage, parsley oil, marjoram, lemon, lime, orange, cis-jasmone, 2,5-dimethyl-4-hydroxy-3(2H)-furanone, 5-ethyl-3-hydroxy-4-methyl-2(5H)-furanone, vanillin, ethyl vanillin, anisaldehyde, 3,4-methylenedioxybenzaldehyde, 3,4-dimethoxybenzaldehyde, 4-hydroxybenzaldehyde, 2-methoxybenzaldehyde, benzaldehyde; cinnamaldehyde, hexyl cinnamaldehyde, alpha-methyl cinnamaldehyde, ortho-methoxy cinnamaldehyde, alpha-amyl cinnamaldehydepropenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptus oil, thymol, cinnamic alcohol, octanol, octanal, decanol, decanal, phenylethyl alcohol, benzyl alcohol, alpha-terpineol, linalool, limonene, citral, maltol, ethyl maltol, anethole, dihydroanethole, carvone, menthone, β-damascenone, ionone, gamma decalactone, gamma nonalactone, gamma undecalactone and combinations of any of the foregoing.

As used herein, the term "sweetening agents" refer to natural or artificial substances that impart or enhance sweet taste of a composition. Sweetening agents include, but are not limited to, monosaccharides, disaccharides, polysaccharides and pharmaceutically acceptable salts thereof, such as xylose, ribose, glucose, mannose, galactose, fructose, sucrose, maltose, invert sugar, partially hydrolyzed starch, corn syrup solids, dihydrochalcones, monellin, steviosides, and glycyrrhizin.

As used herein, the term "humectants" refers to compounds used to reduce the loss of moisture in a composition. Humectants can, for example, impart a moist feeling to a composition when placed in the mouth. Exemplary humectants include, but are not limited to, polyhydric alcohols such as glycerin, sorbitol, xylitol or low molecular weight polyethylene glycols (PEGs).

As used herein, the term "emulsifiers" refers to substances that can stabilize an emulsion formed from a mixture of two or more immiscible liquids. Exemplary emulsifiers include, but are not limited to, poloxamers (difunctional block-polymers terminating in primary hydroxyl groups with molecular weights ranging from 1,000 to above 15,000) such as Poloxamer 407 and Pluraflo L4370, polyacrylic acids such as Pemulen®, vitamin E acetate, vitamin E succinate, and PEGylated Vitamin E.

"Subject" as used herein refers to a human to which the pharmaceutical mouth rinse composition is administered. In some aspects, the subject is a human capable of gargling a liquid. As used herein, "gargling" means the act of bubbling and/or moving liquid around in the subject's mouth, washing said subject's mouth and throat with a liquid kept in motion, and subsequently removing the liquid by spitting out the liquid or by suction.

Compositions

Some embodiments provide a pharmaceutical mouth rinse composition comprising:
about 0.1-1.2% (w/w) Neem oil;
about 8-30% (w/w) Neem extract;
about 3-20% (w/w) *Aloe* extract;
about 0.4-1.5% (w/w) tonicity modifier; and
about 48.65-88.85% (w/w) aqueous carrier. Some embodiments provide a pharmaceutical mouth rinse composition consisting of:
about 0.1-1.2% (w/w) Neem oil;
about 8-30% (w/w) Neem extract;
about 3-20% (w/w) *Aloe* extract;
about 0.4-1.5% (w/w) tonicity modifier; and
about 48.65-88.85% (w/w) aqueous carrier.

Some embodiments provide a pharmaceutical mouth rinse composition comprising:
about 0.25% (w/w) Neem oil;
about 10% (w/w) Neem extract;
about 5% or about 10% (w/w) *Aloe* extract;
about 2-3% (w/w) polysorbate 20;
about 0.5-1.5% (w/w) propylene glycol;
about 0.09-0.1% (w/w) NaCl;
about 0.01-0.05% (w/w) menthol;
about 0.01-0.15% (w/w) thymol;
about 0.05-0.1% (w/w) eucalyptus oil;
about 0.05-0.1% (w/w) wintergreen oil; and water.

Some embodiments provide a pharmaceutical mouth rinse composition consisting of:
about 0.25% (w/w) Neem oil;
about 10% (w/w) Neem extract;
about 5% or about 10% (w/w) *Aloe* extract;
about 2-3% (w/w) polysorbate 20 (w/w);
about 0.5-1.5% (w/w) propylene glycol;
about 0.09-0.1% (w/w) NaCl;
about 0.01-0.05% (w/w) menthol;
about 0.01-0.15% (w/w) thymol;
about 0.05-0.1% (w/w) eucalyptus oil;
about 0.05-0.1% (w/w) wintergreen oil; and water.

In some embodiments, the aqueous carrier comprises water. In some embodiments, the aqueous carrier is water.

In some embodiments, the Neem oil extract is obtained from the seeds of the Neem plant by a suitable extraction method. In some embodiments, the extraction method comprises steam distillation. In some embodiments, the extraction method comprises cold solvent extraction. In some embodiments, the extraction method comprises using supercritical $CO_2$ fluid. In some embodiments, extraction method comprises maceration. In some embodiments, the extraction method comprises cold press extraction. In some embodiments, the extraction method comprises enfleurage. In some embodiments, the extraction method comprises water distillation. In some embodiments, the extraction method comprises hot solvent extraction using a non-polar solvent. Examples of non-polar solvents suitable for the hot solvent extraction process include hexanes, petroleum ether, dichloromethane, xylenes, toluene and ethyl acetate, and mixtures thereof. In some embodiments, the hot solvent extraction is performed at a temperature corresponding to the boiling point of the extraction solvent. In some embodiments, the boiling point of the extraction solvent is about 35° C. to about 140° C., for example, about 35° C. to about 70° C., about 40° C. to about 70° C., about 65° C. to about 80° C., about 80° C. to about 110° C., about 100° C. to about 140° C., about 35° C. to about 50° C., about 50° C. to about 60° C., about 60° C. to about 70° C., about 70° C. to about 80° C., about 80° C. to about 90° C., about 90° C. to about 100° C., about 100° C. to about 110° C., about 110° C. to about 120° C., about 120° C. to about 130° C., or about 130° C. to about 140° C. In some embodiments, the hot solvent extraction is performed at a temperature below 40° C. In some embodiments, the hot solvent extraction is performed at a temperature below 42° C. In some embodiments, the hot solvent extraction is performed at a temperature below 62° C. In some embodiments, the hot solvent extraction is performed at a temperature below 69° C. In some embodiments, the hot solvent extraction is performed at a temperature below 77° C. In some embodiments, the hot solvent extraction is performed at a temperature below 110° C. In some embodiments, the hot solvent extraction is performed at a temperature below 139° C. In some embodiments, the extract obtained in the hot solvent extraction process is concentrated and further partitioned in a polar and a non-polar solvent mixture to yield a polar fraction enriched in nimbolides. Examples of polar solvents suitable for the further partitioning step include methyl alcohol, ethyl alcohol, 1,2-dihydroxyethane, 1,2,3-trihydroxypropane, 1,3-dihydroxypropane and water, and mixtures thereof.

In some embodiments, the Neem leaf extract is obtained by maceration. See, e.g., Zhang et al., Chin. Med. 2018; 13, 20. In some embodiments, the Neem leaf extract is obtained by percolation. In some embodiments, the Neem leaf extract is obtained by reflux extraction. In some embodiments, the Neem leaf extract is obtained by Soxhlet extraction. In some embodiments, the Neem leaf extract is obtained by pressurized liquid extraction. In some embodiments, the Neem leaf extract is obtained by supercritical $CO_2$ fluid extraction. In some embodiments, the Neem leaf extract is obtained by enzyme-assisted extraction. In some embodiments, the Neem leaf extract is obtained by water distillation. In some embodiments, the Neem leaf extract is obtained by steam distillation. In some embodiments, the Neem leaf extract is obtained by microwave-assisted extraction. In some embodiments, the Neem leaf extract is obtained by ultrasound-assisted extraction. In some embodiments, the Neem leaf extract is obtained by pulsed-electric field extraction. In some embodiments, the Neem leaf extract is obtained by decotion in a suitable polar solvent. Examples of polar solvents suitable for decoction include methyl alcohol, ethyl alcohol, 1,2-dihydroxyethane, 1,2,3-trihydroxypropane, 1,3-dihydroxypropane and water, and mixtures thereof. In some embodiments, the decoction process is carried out at a temperature at or around room temperature. As used herein, "room temperature" refers to a temperature range between 20° C. and 30° C. In some embodiments, the decoction process to obtain Neem leaf extract is carried out at about 20° C., about 22° C., about 24° C., about 26° C., about 28° C., and about 30° C. In some embodiments, the Neem leaf extract is obtained by decoction followed by partitioning with a non-polar solvent to remove tannins. Examples of non-polar solvents suitable for the solvent partitioning process to remove tannins include hexanes, petroleum ether, dichloromethane, xylenes, toluene and ethyl acetate, and mixtures thereof. In some embodiments, the *Aloe vera* extract is obtained by maceration. In some embodiments, the *Aloe vera* extract is obtained by percolation. In some embodiments, the *Aloe vera* extract is obtained by reflux extraction. In some embodiments, the *Aloe vera* extract is obtained by Soxhlet extraction. In some embodiments, the *Aloe vera* extract is obtained by pressurized liquid extraction. In some embodiments, the *Aloe vera* extract is obtained by supercritical $CO_2$ fluid extraction. In some embodiments, the *Aloe vera* extract is obtained by enzyme-assisted extraction. In some embodiments, the *Aloe vera* extract is obtained by water distillation. In some embodiments, the *Aloe vera* extract is obtained by steam distillation. In some embodiments, the *Aloe vera* extract is obtained by microwave-assisted extraction. In some embodiments, the *Aloe vera* extract is obtained by ultrasound-assisted extraction. In some embodiments, the *Aloe vera* extract is obtained by pulsed-electric field extraction. In some embodiments, the *Aloe vera* extract is obtained by decoction. In some embodiments, the *Aloe vera* extract is obtained by solvent extraction with a polar solvent. Examples of polar solvents suitable for the solvent extraction process include methyl alcohol, ethyl alcohol, 1,2-dihydroxyethane, 1,2,3-trihydroxypropane, 1,3-dihydroxypropane and water, and mixtures thereof. In some embodiments, the solvent extraction process is carried out at about 20° C. to about 120° C., for example, about 20° C., about 30° C., about 40° C., about 50° C., about 60° C., about 70° C., about 80° C., about 90° C., about 100° C., about 110° C., or about 120° C. In some embodiments, the solvent extraction process is carried out at about room temperature.

In some embodiments, the Neem oil extract, Neem leaf extract and *Aloe vera* extract are mixed with an aqueous carrier. In some embodiments, the amount of Neem oil extract in the aqueous carrier is about 0.05% to about 2% wt/wt. In some embodiments, the amount of Neem oil extract in the aqueous carrier is about 0.08% to about 1.7 wt/wt. In some embodiments, the amount of Neem oil extract in the aqueous carrier is about 0.1% to about 1.5% wt/wt. In some embodiments, the amount of Neem oil extract in the aqueous carrier is about 0.1% to about 1.0% wt/wt. In some embodiments, the amount of Neem oil extract in the aqueous carrier is about 0.1% to about 0.4% wt/wt. In some embodiments, the amount of Neem oil extract in the aqueous carrier is about 0.4% to about 1.2% wt/wt. In some embodiments, the amount of Neem oil extract in the aqueous carrier is about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% wt/wt. In some embodiments, the amount of Neem oil extract in the aqueous carrier is about 0.9% wt/wt. In some embodiments, the amount of Neem oil extract in the aqueous carrier is about 1.0% wt/wt. In some embodiments, the amount of Neem oil extract in the aqueous carrier is about 1.1% wt/wt. In some embodiments, the amount of Neem oil extract in the aqueous carrier is about 0.15% wt/wt. In some embodiments, the amount of Neem oil extract in the aqueous carrier is about 0.25% wt/wt. In some embodiments, the amount of Neem oil extract in the aqueous carrier is about 0.35% wt/wt.

In some embodiments, the amount of Neem leaf extract in the aqueous carrier is about 5% to about 50% wt/wt. In some embodiments, the amount of Neem leaf extract in the aqueous carrier is about 10% to about 30% wt/wt. In some embodiments, the amount of Neem leaf extract in the aqueous carrier is about 8% to about 12% wt/wt. In some embodiments, the amount of Neem leaf extract in the aqueous carrier is about 15% to about 25% wt/wt. In some embodiments, the amount of Neem leaf extract in the aqueous carrier is about 20% to about 30% wt/wt. In some embodiments, the amount of Neem leaf extract in the aqueous carrier is about 5%, about 10%, about 15%, about 20%, about 25%, about 30%, about 35%, about 40%, about 45%, or about 50% wt/wt. In some embodiments, the amount of Neem leaf extract in the aqueous carrier is about 5%, about 6%, about 7%, about 8%, about 9%, about 10%, about 11%, or about 12% wt/wt. In some embodiments, the amount of Neem leaf extract in the aqueous carrier is about 9% wt/wt. In some embodiments, the amount of Neem leaf extract in the aqueous carrier is about 10% wt/wt.

In some embodiments, the amount of Neem leaf extract in the aqueous carrier is about 11% wt/wt.

In some embodiments, the amount of *Aloe vera* extract in the aqueous carrier is about 1% to about 25% wt/wt. In some embodiments, the amount of *Aloe vera* extract in the aqueous carrier is about 3% to about 20% wt/wt. In some embodiments, the amount of *Aloe vera* extract in the aqueous carrier is about 5% to about 15% wt/wt. In some embodiments, the amount of *Aloe vera* extract in the aqueous carrier is about 5% to about 10% wt/wt. In some embodiments, the amount of *Aloe vera* extract in the aqueous carrier is about 15% to about 20% wt/wt. In some embodiments, the amount of *Aloe vera* extract in the aqueous carrier is about 5%, about 10%, about 15%, about 20%, or about 25% wt/wt. In some embodiments, the amount of *Aloe vera* extract in the aqueous carrier is about 1%, about 2%, about 3%, about 4%, about 5%, about 6%, about 7%, about 8%, about 9%, or about 10% wt/wt. In some embodiments, the amount of *Aloe vera* extract in the aqueous carrier is about 3% wt/wt. In some embodiments, the amount of *Aloe vera* extract in the aqueous carrier is about 5% wt/wt. In some embodiments, the amount of *Aloe vera* extract in the aqueous carrier is about 7% wt/wt. In some embodiments, the amount of *Aloe vera* extract in the aqueous carrier is about 10% wt/wt.

In some embodiments, the aqueous carrier comprises a tonicity modifier. In some embodiments, the amount of the tonicity modifier in the aqueous carrier is at about 0.01% to about 0.5% wt/wt. In some embodiments, the amount of the tonicity modifier in the aqueous carrier is at about 0.05% to about 0.2% wt/wt. In some embodiments, the amount of the tonicity modifier in the aqueous carrier is at about 0.07% to about 0.12% wt/wt. In some embodiments, the amount of the tonicity modifier in the aqueous carrier is at about 0.2% to about 0.5% wt/wt. In some embodiments, the amount of the tonicity modifier in the aqueous carrier is at about 0.04%, about 0.05%, 0.06%, about 0.07%, 0.08%, about 0.09%, or about 0.10% wt/wt. In some embodiments, the amount of the tonicity modifier in the aqueous carrier is at about 0.07% wt/wt. In some embodiments, the amount of the tonicity modifier in the aqueous carrier is at about 0.08% wt/wt. In some embodiments, the amount of the tonicity modifier in the aqueous carrier is at about 0.09% wt/wt. In some embodiments, the amount of the tonicity modifier in the aqueous carrier is at about 0.1% wt/wt. In some embodiments, the amount of the tonicity modifier in the aqueous carrier is at about 0.11% wt/wt.

In some embodiments, the tonicity modifier comprises sodium chloride. In some embodiments, the tonicity modifier is sodium chloride. In some embodiments, the tonicity modifier is potassium chloride. In some embodiments, the tonicity modifier is dextose. In some embodiments, the tonicity modifier is mannitol. In some embodiments, the tonicity modifier is glycerin. In some embodiments, the tonicity modifier is calcium chloride. In some embodiments, the tonicity modifier is magnesium chloride.

In some embodiments, the aqueous carrier further comprises one or more flavoring agents. In some embodiments, the total amount of the one or more flavoring agents in the aqueous carrier is about 0.01% to about 0.5% wt/wt. In some embodiments, the total amount of the one or more flavoring agents in the aqueous carrier is about 0.1% to about 0.3% wt/wt. In some embodiments, the total amount of the one or more flavoring agents in the aqueous carrier is about 0.3% to about 0.5% wt/wt. In some embodiments, the total amount of the one or more flavoring agents in the aqueous carrier is about 0.2% to about 0.3% wt/wt. In some embodiments, the total amount of the one or more flavoring agents in the aqueous carrier is about 0.08%, about 0.1%, about 0.12%, about 0.14%, about 0.16%, about 0.18%, about 0.2%, about 0.25%, about 0.28%, or about 0.3% wt/wt. In some embodiments, the total amount of the one or more flavoring agents in the aqueous carrier is about 0.15%. In some embodiments, the total amount of the one or more flavoring agents in the aqueous carrier is about 0.25%. In some embodiments, the total amount of the one or more flavoring agents in the aqueous carrier is about 0.35%.

In some embodiments, the one or more flavoring agents are selected from menthol, thymol, methyl salicylate, eucalyptus oil, wintergreen oil, peppermint oil, spearmint oil, cinnamon oil, citrus oil, anise oil, clove oil, caraway oil, pimento oil and nutmeg oil. In some embodiments, the one or more flavoring agents are selected from menthol, thymol, eucalyptus oil, wintergreen oil, cinnamon oil, and clove oil. In some embodiments, the one or more flavoring agents are selected from menthol, thymol, eucalyptus oil and wintergreen oil. In some embodiments, the amount of menthol in the aqueous carrier is about 0.01% to about 0.15% wt/wt. In some embodiments, the amount of menthol in the aqueous carrier is about 0.02% to about 0.08% wt/wt. In some embodiments, the amount of menthol in the aqueous carrier is about 0.03% to about 0.05% wt/wt. In some embodiments, the amount of menthol is about 0.03% wt/wt. In some embodiments, the amount of menthol is about 0.04% wt/wt. In some embodiments, the amount of menthol is about 0.05% wt/wt. In some embodiments, the amount of thymol in the aqueous carrier is about 0.01% to about 0.2% wt/wt. In some embodiments, the amount of thymol in the aqueous carrier is about 0.05% to about 0.15% wt/wt. In some embodiments, the amount of thymol in the aqueous carrier is about 0.07% to about 0.12% wt/wt. In some embodiments, the amount of thymol is about 0.08% wt/wt. In some embodiments, the amount of thymol is about 0.09% wt/wt. In some embodiments, the amount of thymol is about 0.1% wt/wt. In some embodiments, the amount of eucalyptus oil in the aqueous carrier is about 0.01% to about 0.15% wt/wt. In some embodiments, the amount of eucalyptus oil in the aqueous carrier is about 0.04% to about 0.07% wt/wt. In some embodiments, the amount of eucalyptus oil in the aqueous carrier is about 0.08% to about 0.15% wt/wt. In some embodiments, the amount of eucalyptus oil is about 0.04%. In some embodiments, the amount of eucalyptus oil is about 0.06% wt/wt. In some embodiments, the amount of eucalyptus oil is about 0.08%. In some embodiments, the amount of wintergreen oil in the aqueous carrier is about 0.01% to about 0.15% wt/wt. In some embodiments, the amount of wintergreen oil in the aqueous carrier is about 0.04% to about 0.07% wt/wt. In some embodiments, the amount of wintergreen oil in the aqueous carrier is about 0.08% to about 0.15% wt/wt. In some embodiments, the amount of wintergreen oil is about 0.04% wt/wt. In some embodiments, the amount of wintergreen oil is about 0.06% wt/wt. In some embodiments, the amount of wintergreen oil is about 0.08% wt/wt.

In some embodiments, the aqueous carrier further comprises one or more sweetening agents. In some embodiments, the total amount of the one or more sweetening agents in the aqueous carrier is about 0.01% to about 2.0% wt/wt. In some embodiments, the total amount of the one or more sweetening agents in the aqueous carrier is about 0.1% to about 1.0% wt/wt. In some embodiments, the total amount of the one or more sweetening agents in the aqueous carrier is about 0.05% to about 0.5% wt/wt. In some embodiments, the total amount of the one or more sweetening agents in the aqueous carrier is about 0.1% to about 0.3% wt/wt. In some embodiments, the total amount of the one or more sweetening agents in the aqueous carrier is about 0.3% to about 0.5% wt/wt. In some embodiments, the total amount of the one or more sweetening agents in the aqueous carrier is about 0.5% to about 1% wt/wt. In some embodiments, the total amount of the one or more sweetening agents in the aqueous carrier is about 1% to about 2% wt/wt. In some embodiments, the one or more sweetening agents are selected from saccharin, aspartame, acesulfame-K, sucralose, neohesperidine, dihydrichalcone, sorbitol, sucrose, glucose, dextrose, corn syrup, erythritol, xylitol, isomalt, maltitol, mannitol, and lactitol. In some embodiments, the one or more sweetening agents are selected from saccharin, aspartame, sorbitol, sucrose, glucose, dextrose, xylitol, mannitol, and lactitol. In some embodiments, the one or more sweetening agents are selected from saccharin, aspartame, and sorbitol.

In some embodiments, the aqueous carrier further comprises one or more humectants. In some embodiments, the total amount of the one or more humectants in the aqueous carrier is about 0.5% to about 3.5% wt/wt. In some embodiments, the total amount of the one or more humectants in the aqueous carrier is about 0.8% to about 2% wt/wt. In some embodiments, the total amount of the one or more humectants in the aqueous carrier is about 0.5% to about 1.5% wt/wt. In some embodiments, the total amount of the one or more humectants in the aqueous carrier is about 0.8% wt/wt. In some embodiments, the total amount of the one or more humectants in the aqueous carrier is about 1% wt/wt. In some embodiments, the total amount of the one or more humectants in the aqueous carrier is about 1.2% wt/wt. In some embodiments, the total amount of the one or more humectants in the aqueous carrier is about 1.5% wt/wt. In some embodiments, the total amount of the one or more humectants in the aqueous carrier is about 2%. In some embodiments, the total amount of the one or more humectants in the aqueous carrier is about 3%. In some embodiments, the one or more humectants are selected from glycerin, ethylene glycol, propylene glycol, butylene glycol, hexylene glycol, sorbitol, hydrogenated corn syrups, and hydrogenated starch hydrolysates. In some embodiments, the one or more humectants are selected from glycerin, ethylene glycol, propylene glycol, and sorbitol. In some embodiments, the humectant is propylene glycol. In some embodiments, the aqueous carrier further comprises one or more emulsifiers. In some embodiments, the total amount of the one or more emulsifiers in the aqueous carrier is about 1% to about 5% wt/wt. In some embodiments, the total amount of the one or more emulsifiers in the aqueous carrier is about 2% to about 3% wt/wt. In some embodiments, the total amount of the one or more emulsifiers in the aqueous carrier is about 2% to about 2.5% wt/wt. In some embodiments, the total amount of the one or more emulsifiers in the aqueous carrier is about 2%. In some embodiments, the total amount of the one or more emulsifiers in the aqueous carrier is about 2.2%. In some embodiments, the total amount of the one or more emulsifiers in the aqueous carrier is about 2.5%. In some embodiments, the one or more emulsifiers are selected from a polysorbate, a polyethylene glycol (PEG), a polyphosphate, and a fatty acid sulfate. In some embodiments, the one or more emulsifiers are selected from polysorbate 20, polysorbate 80, Poloxamer 338, Poloxamer 407, PEG 20, PEG 40, PEG 1000, sodium tripolyphosphate, and sodium lauryl sulfate. In some embodiments, the one or more emulsifiers are selected from sodium lauryl sulfate, polysorbate 80 and polysorbate 20. In some embodiments, the one or more emulsifiers are selected from polysorbate 80 and polysorbate 20. In some embodiments, the emulsifier is polysorbate 20.

In some embodiments, the pharmaceutical mouth rinse composition comprises a mixture comprising about 0.1% to about 1.0% wt/wt of Neem oil extract, about 10% to 30% wt/wt of Neem leaf extract, about 5% to about 20% wt/wt of *Aloe vera* extract and about 60% to about 80% wt/wt of an aqueous carrier. In some embodiments, the aqueous carrier comprises about 0.05% to about 0.2% wt/wt of a tonicity modifier. In some embodiments, the aqueous carrier comprises about 0.1% to about 0.5% wt/wt of one or more flavoring agents, about 0.02% to about 0.5% wt/wt of one or more sweetening agents, about 0.8% to about 2% wt/wt of one or more humectants, and about 2% to about 3% wt/wt of one or more emulsifiers. In some embodiments, the pharmaceutical mouth rinse composition comprises about 0.25% wt/wt of Neem oil extract, about 10% wt/wt of Neem leaf extract, about 5% wt/wt of *Aloe vera* extract in an aqueous carrier comprising about 0.09% wt/wt of sodium chloride, about 0.04% wt/wt of menthol, about 0.09% wt/wt of thymol, about 0.06% wt/wt of eucalyptus oil, about 0.06% wt/wt of wintergreen oil, about 1% wt/wt of propylene glycol, about 2.2% of polysorbate 20, and about 81% of distilled deionized water. In some embodiments, the pharmaceutical mouth rinse composition comprises about 0.25% wt/wt of Neem oil extract, about 10% wt/wt of Neem leaf extract, about 10% wt/wt of *Aloe vera* extract in an aqueous carrier comprising about 0.1% wt/wt of sodium chloride, about 0.04% wt/wt of menthol, about 0.09% wt/wt of thymol, about 0.06% wt/wt of eucalyptus oil, about 0.06% wt/wt of wintergreen oil, about 2.2% of polysorbate 20, about 1% propylene glycol, and about 76% of distilled deionized water.

In some embodiments, the pharmaceutical mouth rinse composition comprises about 0.25% (w/w) Neem oil; about 10% (w/w) Neem extract; about 5-10% (w/w) *Aloe* extract; about 0.1% (w/w) NaCl; and about 79.65-84.65% (w/w) aqueous carrier. In some embodiments, the pharmaceutical mouth rinse composition consists of: about 0.25% (w/w) Neem oil; about 10% (w/w) Neem extract; about 5% (w/w) *Aloe* extract; about 0.1% (w/w) NaCl; and about 79.65-84.65% (w/w) aqueous carrier. In some embodiments, the aqueous carrier is water. In some embodiments, the aqueous carrier comprises water. In some embodiments, the aqueous carrier consists of water and from 1-5 of any combination of flavoring agents, sweetening agents, humectants, and emulsifiers.

Methods of Use

In some embodiments, the pharmaceutical mouth rinse composition is used in the treatment or prevention of a coronaviridae infection in a subject in need thereof. In some embodiments, the methods comprise preventing a coronaviridae infection. In some embodiments, the methods comprise treating a coronaviridae infection. In some embodiments, the methods consist essentially of preventing a coronaviridae infection. In some embodiments, the methods consist essentially of treating a coronaviridae infection.

In some embodiments, the pharmaceutical mouth rinse composition is used in the inhibition of coronaviridae replication in a subject in need thereof. In some embodiments, the coronaviridae replication is inhibited by about 25% to about 99% after about 7 to about 21 days of administration of the composition. In some embodiments, the pharmaceutical mouth rinse composition is used in the inhibition of coronaviridae replication in a subject in need thereof. In some embodiments, the coronaviridae replication is inhibited by about 25% to about 99% after about 7 to about 15 days of administration of the composition.

For example, coronaviridae replication is inhibited by about 25% to about 50%, about 35% to about 60%, about 50% to about 75%, about 65% to about 90%, about 75% to about 99%, or any value in between.

In some embodiments, the coronaviridae is a human coronavirus. In some embodiments, the coronaviridae is 229E, NL63, OC43, HKU1, SARS-Cov1, SARS-Cov2, or MERS-Cov. In some embodiments, the coronaviridae is SARS-Cov1, SARS-Cov2, or MERS-Cov. In some embodiments, the coronaviridae is SARS-Cov1. In some embodiments, the coronaviridae is SARS-Cov2. In some embodiments, the coronaviridae is MERS-Cov.

In some embodiments, the method of treating or preventing a coronaviridae infection in the subject comprises administering the pharmaceutical mouth rinse composition of any of the foregoing embodiments to the subject. In some embodiments, the method of inhibiting coronaviridae replication in the subject comprises administering the pharmaceutical mouth rinse composition of any of the foregoing embodiments to the subject. In some embodiments, the pharmaceutical mouth rinse composition is administered to the subject by gargling. In some embodiments, the administering comprises gargling about 5-30 mL of the pharmaceutical mouth rinse composition. In some embodiments, the administering comprises gargling about 15-25 mL of the pharmaceutical mouth rinse composition. In some embodiments, the administering comprises gargling about 10-20 mL of the pharmaceutical mouth rinse composition. In some embodiments, the administering comprises gargling the pharmaceutical mouth rinse composition for about 20-80 seconds. In some embodiments, the administering comprises gargling the pharmaceutical mouth rinse composition for about 40-60 seconds. In some embodiments, the administering comprises gargling the pharmaceutical mouth rinse composition for about 20-30 seconds.

In some embodiments, the pharmaceutical mouth rinse composition is administered to the subject in need thereof by performing nasal lavage with the said composition.

In some embodiments, the pharmaceutical mouth rinse composition is administered 1-6 times per day. In some embodiments, the pharmaceutical mouth rinse composition is administered 2-4 times per day. In some embodiments, the pharmaceutical mouth rinse composition is administered once per day. In some embodiments, the pharmaceutical mouth rinse composition is administered twice per day. In some embodiments, the pharmaceutical mouth rinse composition is administered 3 times per day. In some embodiments, the pharmaceutical mouth rinse composition is administered 4 times per day. In some embodiments, the pharmaceutical mouth rinse composition is administered each day for 3-30 days. In some embodiments, the pharmaceutical mouth rinse composition is administered each day for 6-14 days. In some embodiments, the pharmaceutical mouth rinse composition is administered each day for 6 day, 7 days, 8 days, 9 days, 10 days, 11 days, 12 days, 13 days, or 14 days. In some embodiments, the pharmaceutical mouth rinse composition is administered each day for 14 days. In some embodiments, the pharmaceutical mouth rinse composition is administered each day for 7 days. In some embodiments, the pharmaceutical mouth rinse composition is administered each day for 21 days.

EXAMPLES

Example 1

Preparation of Neem Oil Extract

*Azadirachta indica* (Neem) oil extract was obtained from kernels of Neem seeds by the hot extraction method. The finely ground Neem seed kernel (500 grams) was stirred in two liters of hexanes at 40° C. for 2 to 3 hours to extract the Neem oil. After completion of the extraction, the suspension was filtered by vacuum filtration. The liquid containing the Neem oil was concentrated by evaporation using a rotary evaporator to yield approximately 212 grams of oil. No further purification of the Neem oil extract was performed.

Example 2

Preparation of Neem Leaf Extract

*Azadirachta indica* (Neem) leaf extract was obtained using maceration. In brief, the Neem leaves (500 grams) were ground in five liters of glycerin and stored at room temperature for two weeks. The solvent containing the Neem leaf extract was decanted or filtered to remove the solid plant material. No further purification of the Neem leaf extract was performed.

Example 3

Preparation of *Aloe vera* Extract

*Aloe vera* extract was prepared using maceration. Briefly, approximately 500 grams of *Aloe vera* leaves were soaked in one liter of glycerin for two weeks at room temperature. The resulting liquid was then decanted and filtered. No further purification of the *Aloe vera* extract was performed.

Example 4

Preparation of Mouth Rinse A

Mouth Rinse A was prepared by adding 0.25 g of Neem oil, 10 g of Neem leaf extract, 5 g of *Aloe vera* extract, obtained according to Examples 1-3 above, to 81.145 g of an aqueous carrier in a 1-L glass bottle. Upon adding the plant extracts to the aqueous carrier, the resulting mixture was stirred using a magnetic stirrer for 10 min to ensure complete mixing. The aqueous carrier was prepared by mixing 40 mg of menthol, 60 mg of thymol, 90 mg of eucalyptus oil, 60 mg of wintergreen oil, 60 mg of sweetener, 1 g of humectant, 2.2 gram emulsifier and 0.09 g of NaCl.

Example 5

Preparation of Mouth Rinse B

Mouth Rinse B was prepared by adding 0.25 g of Neem oil, 10 g of Neem leaf extract, 10 g of *Aloe vera* extract, obtained according to Examples 1-3 above, to 76.14 g of an aqueous carrier in a 1-L glass bottle. Upon adding the plant extracts to the aqueous carrier, the resulting mixture was stirred using a magnetic stirrer for 10 min to ensure complete mixing. The aqueous carrier was prepared by mixing 40 mg of menthol, 60 mg of thymol, 90 mg of eucalyptus oil, 60 mg of wintergreen oil, 60 mg of sweetener, 1 g of humectant, 2.2 gram of emulsifier and 0.1 g of NaCl.

Example 6

Placebo-Controlled, Double-Blind Clinical Trial of Gargling Agents in Reducing Intraoral Viral Load Among COVID-19 Patients Subjects who have tested positive with a COVID-19 infection within 7 days of the start of the trial using a suitable laboratory test (e.g., nasal swab PCR test), between the ages of 18-65 years may be included in the clinical trial. Subjects exhibiting mild to moderate symptoms consistent with an upper respiratory tract viral infection (e.g., sneezing, sore throat, dry cough, runny nose) may also be included. However, those subjects with low Glasgow coma scores, intubated subjects, and/or a recent history of radiotherapy or chemotherapy are excluded.

Enrolled subjects are divided into two groups, a treatment group and a control group. The treatment group will gargle 10-20 mL of the pharmaceutical mouth rinse composition prepared as described in Example 4 above for 20-30 s, three times daily (with at least 3 hours between each use) for 6-14 days. All subjects will be evaluated by a quantitative polymerase chain reaction (qPCR) assay throughout the duration of the trial and followed for 7 days post-administration.

A number of embodiments of the present application have been described. Nevertheless, it will be understood that various modifications may be made without departing from the spirit and scope of the disclosure. Accordingly, other embodiments are within the scope of the following claims.

What is claimed is:

1. A pharmaceutical mouth rinse composition comprising:
about 0.1-1.2% (w/w) Neem oil;
about 9% (w/w) Neem extract;
about 3-20% (w/w) *Aloe* extract;
about 0.05-0.15% (w/w) tonicity modifier; and
about 48.65-88.85% (w/w) aqueous carrier.

2. The composition of claim 1, wherein the composition has a pH of about 6.0 to about 8.0.

3. The composition of claim 1, wherein the composition is one of a solution and an emulsion.

4. The composition of claim 1, wherein the composition comprises:
about 0.1% to about 0.4% Neem oil;
about 9% Neem extract;
about 5% to about 10% *Aloe* extract;
about 0.09% tonicity modifier, wherein the tonicity modifier is sodium chloride; and
about 60% to about 80% aqueous carrier.

5. The composition of claim 4, wherein the aqueous carrier comprises water and one or more components selected from: flavoring agents, sweetening agents, humectants, and emulsifiers.

6. The composition of claim 5, wherein the one or more flavoring agents are selected from menthol, thymol, methyl salicylate, *eucalyptus* oil, wintergreen oil, peppermint oil, spearmint oil, cinnamon oil, citrus oil, anise oil, clove oil, caraway oil, pimento oil and nutmeg oil.

7. The composition of claim 6, wherein the aqueous carrier comprises about 0.03% to about 0.05% menthol, about 0.05% to about 0.15% thymol, about 0.04% to about 0.07% *eucalyptus* oil, or about 0.04% to about 0.07% wintergreen oil; or a combination of any of the foregoing.

8. The composition of claim 5, wherein the one or more sweetening agents are selected from saccharin, aspartame, acesulfame-K, sucralose, neohesperidin dihydrochalcone (NHDC), sorbitol, sucrose, glucose, dextrose, corn syrup, erythritol, xylitol, isomalt, maltitol, mannitol, and lactitol.

9. The composition of claim 5, wherein the one or more humectants are selected from glycerin, ethylene glycol, propylene glycol, butylene glycol, hexylene glycol, sorbitol, hydrogenated corn syrups, and hydrogenated starch hydrolysates.

10. The composition of claim 5, wherein the one or more emulsifiers are selected from a polysorbate, a polyethylene glycol (PEG), a polyphosphate, and a fatty acid sulfate.

11. The composition of claim 5, wherein the aqueous carrier comprises water and about 0.1% to about 0.5% flavoring agents, about 0.02% to about 0.5% sweetening agents, about 0.8% to about 2% humectants, and about 2% to about 3% emulsifiers.

12. A pharmaceutical mouth rinse composition consisting of:
about 0.25% (w/w) Neem oil;
about 10% (w/w) Neem extract;
about 5% or about 10% (w/w) *Aloe* extract;
about 2-3% (w/w) polysorbate 20;
about 0.5-1.5% (w/w) propylene glycol;
about 0.09-0.1% (w/w) sodium chloride;
about 0.01-0.05% (w/w) menthol;
about 0.01-0.15% (w/w) thymol;
about 0.05-0.1% (w/w) *eucalyptus* oil;
about 0.05-0.1% (w/w) wintergreen oil; and
water.

13. The composition of claim 12, wherein the composition has a pH of about 6.0 to about 8.0.

14. The composition of claim 12, wherein the composition is one of a solution or an emulsion.

15. The composition of claim 12, wherein the amount of *Aloe vera* extract is about 10% (w/w).

16. The composition of claim 12, wherein the amount of menthol is about 0.04% (w/w).

17. The composition of claim 12, wherein the amount of thymol is about 0.08% (w/w).

18. The composition of claim 12, wherein the amount of *eucalyptus* oil is about 0.06% (w/w).

19. The composition of claim 12, wherein the amount wintergreen oil is about 0.06% (w/w).

* * * * *